US009415023B2

(12) United States Patent
McLellan et al.

(10) Patent No.: US 9,415,023 B2
(45) Date of Patent: *Aug. 16, 2016

(54) COMPOSITIONS COMPRISING TERPENE COMPOUNDS FOR TREATING NEGATIVE SENSORY PHENOMENA (75) Inventors: Alexander McLellan, Halifax (CA); Frank Greenway, Baton Rouge, LA (US)

(73) Assignees: NeuroQuest Inc., Halifax, Nova Scotia (CA); Board Of Supervisors Of Louisana State University And Agricultural And Mechanical College Pennington Biomedical Research Center, Baton Rouge, LA (US)

( * ) Notice: Subject to any disclaimer, the term of this patent is extended or adjusted under 35 U.S.C. 154(b) by 195 days.

This patent is subject to a terminal disclaimer.

(21) Appl. No.: 13/058,762

(22) PCT Filed: Aug. 13, 2009

(86) PCT No.: PCT/CA2009/001114
§ 371 (c)(1),
(2), (4) Date: Feb. 11, 2011

(87) PCT Pub. No.: WO2010/017626
PCT Pub. Date: Feb. 18, 2010

(65) Prior Publication Data
US 2011/0144191 A1    Jun. 16, 2011

Related U.S. Application Data (60) Provisional application No. 61/088,508, filed on Aug. 13, 2008.

(51) Int. Cl.
*A61K 31/045* (2006.01)
*A61K 31/121* (2006.01)
*A61K 31/122* (2006.01)
*A61K 31/22* (2006.01)
*A61K 31/351* (2006.01)

(52) U.S. Cl.
CPC ............. *A61K 31/045* (2013.01); *A61K 31/121* (2013.01); *A61K 31/122* (2013.01); *A61K 31/22* (2013.01); *A61K 31/351* (2013.01)

(58) Field of Classification Search
None
See application file for complete search history.

(56) References Cited

U.S. PATENT DOCUMENTS

| 4,311,617 | A | 1/1982 | Ansari |
| 4,579,677 | A | 4/1986 | Hooper |
| 4,826,875 | A | 5/1989 | Chiesi |
| 4,923,685 | A | 5/1990 | Wuelkhitz |
| 4,940,583 | A | 7/1990 | Thompson |
| 5,260,313 | A * | 11/1993 | Frome ............ 514/552 |
| 5,770,738 | A | 6/1998 | Banholzer et al. |
| 6,248,307 | B1 * | 6/2001 | Borneman et al. ........... 424/451 |
| 2003/0092636 | A1 | 5/2003 | Silberstein |
| 2003/0224072 | A1 | 12/2003 | Frome |
| 2005/0090557 | A1 | 4/2005 | Muhammad et al. |
| 2005/0112183 | A1 | 5/2005 | Galer |
| 2006/0004050 | A1 * | 1/2006 | Speicher et al. ............. 514/317 |
| 2006/0222690 | A1 | 10/2006 | Bley |
| 2010/0099772 | A1 | 4/2010 | Bean |
| 2011/0144191 | A1 | 6/2011 | McLellan |
| 2013/0267571 | A1 | 10/2013 | Reed |
| 2014/0357725 | A1 | 12/2014 | Weaver |

FOREIGN PATENT DOCUMENTS

| WO | 93/17695 A1 | 9/1993 |
| WO | 02/053151 | 7/2002 |
| WO | 03/049726 | 6/2003 |
| WO | 2006014788 | 2/2006 |
| WO | 2007/095631 A2 | 8/2007 |
| WO | WO 2008063603 A2 * | 5/2008 |
| WO | 2008/095297 A1 | 8/2008 |
| WO | WO 2008095297 A1 * | 8/2008 |
| WO | 2008/108825 A2 | 9/2008 |
| WO | 2010/017626 | 2/2010 |
| WO | 2010/057295 A9 | 5/2010 |
| WO | 2012/034232 | 3/2012 |
| WO | 2013/008093 | 1/2013 |

OTHER PUBLICATIONS

U.S. Appl. No. 12/537,095, filed Aug. 2009, McLellan.*
U.S. Appl. No. 13/822,826, filed Mar. 2013, Reed.*
Vendruscolo et al, Antiinflammatory and antinociceptive activities of zingiber officinale roscoe essential oil in experimental animal models, Ind J Pharm, vol. 38, No. 1, pp. 58-59, 2006.*
Pittler et al., Temporary relief of postherpetic neuralgia pain with topical geranium oil, Am. J. Med., vol. 115, pp. 586-587, Nov. 2003.*
A definition of "nociceptive" from a medical dictionary online available at http://medical-dictionary.thefreedictionary.com/nociceptive on Mar. 27, 2014.*
Haiyan et al., Antinociceptive effects of matrine on neuropathic pain induced by chronic constriction injury, Pharm Biol. Jul. 2013;51(7):844-50, Epub Apr. 29, 2013 (Abstract).*
Porter, Pure Appl Chem, (1969), 20: 449-481.*
Supplementary European Search Report from EP 09806221, dated Jan. 13, 2012.
Kalso, E Sodium Channel Blockers in Neuropathic Pain, Current Pharmaceutical Design, vol. 11, No. 23, Sep. 2005, pp. 3005-3011(7).

(Continued)

*Primary Examiner* — Svetlana M Ivanova
(74) *Attorney, Agent, or Firm* — Barnes & Thornburg LLP (57) ABSTRACT Compositions comprising terpene compounds for the treatment of negative sensory phenomena (NSP). Negative sensory phenomena is characterized by a decreased ability to sense light touch, pin prick, vibration, temperature, pain and/or reduced proprioception. The terpene compounds are preferably aromatic terpene compounds such as geraniol and citronellol and analogs thereof. The terpenes may also be used in combination. The terpenes are derived form plant essential oils or are manufactured synthetically.

10 Claims, 3 Drawing Sheets

(56) References Cited

OTHER PUBLICATIONS

Sindrup, Soren H.; Otto, Marit; Finnerup, Nanna B. Jensen, Troels S.Antidepressants in the Treatment of Neuropathic Pain Basic & Clinical Pharmacology & Toxicology, vol. 96, No. 6, Jun. 2005, pp. 399-409(11).
Jensen TS. Anticonvulsants in neuropathic pain: rationale and clinical evidence. Eur J Pain. 2002;6 Suppl A:61-8.
Kingery WS. A critical review of controlled clinical trials for peripheral neuropathic pain and complex regional pain syndromes. Pain 1997;73:123-139.
Elon Eisenberg, MD; Ewan D. McNicol, RPh; Daniel B. Can, MD Efficacy and Safety of Opioid Agonists in the Treatment of Neuropathic Pain of Nonmalignant Origin JAMA. 2005;293:3043-3052.
Fromm GH. Baclofen as an adjuvant analgesic. J Pain Symptom Management 1994;9(8):500-509.
Eide K, Stubhaug A, Oye I, Breivik H. Continuous subcutaneous administration of the N-methyl-D-aspartic acid (NMDA) receptor antagonist ketamine in the treatment of postherpetic neuralgia. Pain 1995;61(2):221-8.
Sindrup SH, Jensen TS. Efficacy of pharmacological treatments of neuropathic pain: an update and effect related to mechanism of drug action. Pain 1999;83(3):389-400.
Kronenberg RH. Ketamine as an analgesic: parenteral, oral, rectal, subcutaneous, transdermal and intranasal administration. J Pain Palliat Care Pharmacother. 2002;16(3):27-35.
Greenway FL, Frome BM, Engels TM 3rd, McLellan A. Temporary relief of postherpetic neuralgia pain with topical geranium oil. Am J Med Nov. 2003; 115(7):586-7.
Vendruscolo A, Takaki I, Bersani-Amado LE, Dantas JA, Bersani-Amado CA, Cuman R K.N Antiinflammatory and antinociceptive activities of zingiber officinale roscoe essential oil in experimental animal models. Ind J Pharm vol. 38 No. 1 p. 58-59 2006.
Nicoletta Galeotti, Lorenzo Di Cesare Mannelli, Gabriela Mazzanti,Alessandro Bartolini, Carla Ghelardini Menthol: a natural analgesic compound Neuroscience Letters 322 (2002) 145-148 Neurology 2005;65:812-819.
New Jersey Dept of Health Hazardous Substance Fact Sheet Jul. 1999 #0052.
http://Toxnet.nlm.nih.gov CASRN:555-10-2, Oct. 24, 2011.
Johnston, G.A.R. GABA Receptor Channel Pharmacology. Current Pharmaceutical Design 2005, 11, 1867-1885.
Non-Final Office Action, U.S. Appl. No. 12/537,095, dated May 4, 2012, 17 pages.
Final Office Action, U.S. Appl. No. 12/537,095, dated Apr. 22, 2013, 12 pages.
Kingery, Wade S. "A critical review of controlled clinical trials for peripheral neuropathic pain and complex regional pain syndromes." Pain 73.2 (1997): 123-139.
Kvarnström, Ann, et al. "The effectiveness of intravenous ketamine and lidocaine on peripheral neuropathic pain." Acta anaesthesiologica scandinavica47.7 (2003): 868-877.
McCleane, Gary. "Topical application of doxepin hydrochloride, capsaicin and a combination of both produces analgesia in chronic human neuropathic pain: a randomized, double-blind, placebo-controlled study." British journal of clinical pharmacology 49.6 (2000): 574-579.
Nalamachu, Srinivas, et al. "A comparison of the lidocaine patch 5% vs naproxen 500 mg twice daily for the relief of pain associated with carpal tunnel syndrome: a 6-week, randomized, parallel-group study." Medscape General Medicine 8.3 (2006): 33.
Delellis, Salvatore L., Dale H. Carnegie, and Thomas J. Burke. "Improved sensitivity in patients with peripheral neuropathy: effects of monochromatic infrared photo energy." Journal of the American Podiatric Medical Association95.2 (2005): 143-147.
Shellie, Robert A., and Philip J. Marriott. "Comprehensive two-dimensional gas chromatography-mass spectrometry analysis of Pelargonium graveolens essential oil using rapid scanning quadrupole mass spectrometry." Analyst128.7 (2003): 879-883.
Suekawa et al. "Pharmacological studies on ginger. I. Pharmacological actions of pungent constitutents,(6)-gingerol and (6)-shogaol." Journal of pharmacobio-dynamics 7.11 (1984): 836-848.
Alessandra T. Peana et al., "(−) Linalool produces antinociception in two experimental models of pain", European journal of pharmacology, vol. 460, No. 1, Jan. 1, 2003, pp. 37-41, XP055172891, ISSN: 0014-2999, DOI: 10.1016/S0014-2999(02)02856-X.
Silva-Santos, A. et al., "Analysis of uses of essential oils and terpenics/terpenoids compounds by pharmaceutical industry through USPTO granted patents", Rev. Bras. Pl. Med. 2008, vol. 10, No. 1, pp. 8-15.
Abena et al., "Comparative Chemical and Analgesic Properties of Essential Oils of Cymonpogon Nardus (L) Rendle of Benin and Congo", African Journal of Traditional, AJTCAM/African Networks on Ethnomedicines 2007, vol. 4, No. 3, pp. 267-272.
Ortiz, Mario et al., "The combination of naproxen and citral reduces nociception and gastric damage in rats", Archives of Pharmacal Research, vol. 33, No. 10, Oct. 2010, pp. 1691-1697.
Stotz, Stephanie et al., "Citral Sensing by TRANSient Receptor Potential Channels in Dorsal Root Ganglion Neurons", PLOS ONE, Public Library of Science, US, vol. 3, No. 5, May 7, 2008.
Gunthorpe, M et al., "Clinical development of TRPV1 antagonists: targeting a pivotal point in the pain pathway", Drug Discovery Today, vol. 14, No. 1-2, Jan. 1, 2009, pp. 56-67.WO2007095631.
Ghelardini, C. et al., "Local Anaesthetic Activity of Monoterpene and Phenylpropoanes of Essential Oils", Planta Med., vol. 67, p. 564-566, 2001.
Woolf et al., "Neuropathic pain: aetilogy, symptoms, mechanisms, and management", Lancet 1999; 353; 1959-64.
Zhang et al., "The Balance Between Excitation and Inhibition and Functional Sensory Processing in the Somatosensory Cortex", International Review of Neurobiology, 2011, vol. 97, DOI: 10.1016/B978-0-12-385198-7.00012-6, pp. 305-333.
Brown et al., "Abnormalities of the balance between inhibition and excitation in the motor cortex of patients with cortical myoclonus", Brain (1996), 119, 309-317.
Moriera et al., "Effects of terpineol on the compound action potential of the rat sciatic nerve", Brazilian Journal of Medicine and Biological Research (2001) 34:1337-1340.
Ippolito et al., "Tyrosine Phosphorylation of Kir3.1 in Spinal Cord is Induced by Acute Inflammation, Chronic Neuropathic Pain, and Behavioral Stress", J. Biol. Chem. 2005, 280:41683-41693, Oct. 13, 2005.
Beekwilder et al/. "Kv1.1 Channels of Dorsal Root Ganglion Neurons are Inhibited by n-Butyl-p-aminobenzoate, a Promising Anesthetic for the Treatment of Chronic Pain", The Journal of Pharmacology and Experimental Therapeutics, vol. 304, No. 2, pp. 531-538, 2003.
Cooper et al., "Ion channel genes and human neurological disease: Recent progress, prospects, and challenges", Proc. Natl. Acad. Sci. vol. 96, pp. 4759-4766, Apr. 1999.
Devor, Marshall, "Sodium Channels and Mechanisms of Neuropathic Pain", The Journal of Pain, vol. 7, No. 15 (January), Supplement 1, 2006: pp. S3-S12.
Olsen et al., "Progress in Epilepsy Research GABA and Epieptogenesis", Epilepsia, 38(4):399-407, 1997.
Cobos et al., "Mice lacking Dix1 show subtype-specific loss of interneurons, reduced inhibition and epilepsy", Nature Neuroscience vol. 8, No. 8, Aug. 2005.
Laumonnier et al., "X-Limnked Mental Retardation and Autism are Associated with a Mutation in the NLGN4 Gene, a Member of the Neuroligin Family", Am. J. Hum. Genet. 74:552-557, 2004.
Dani et al., "Reduced cortical activity due to a shift in the balance between excitation and inhibition in a mouse model of Rett Syndrome", 12560-12565, PNAS, Aug. 30, 2005, vol. 102, No. 35.
Nickell et al., "Evidence for GABAB-mediated inhibition of Transmission from the olfactory nerve to mitral cells in the rat olfactory bulb", Brain Res Bull., 1994;35(2); 119-23.
Cates et al., "2,2'-Phthaloyl-, 2,2'-isophthaloyl-, and 2,2'-terephthaloylbis{1,1,1-trimethylhydrazinium]dihydroxide, bis(inner salts); synthesis, partition coefficients, toxicity and effect on ganglionic transmission", J Pharm Sci. Apr. 1986;75(4)"407-9.

(56) References Cited

OTHER PUBLICATIONS

Excerpt from Mechanisms and Mediators of Neuropathic Pain, 2002 (textbook).
Pommer et al., "Industrial synthesis of terpene compounds", Pure and Applied Chemistry 43.3-4 (1975): 527-551.
Solis et al., "Antibacterial and Antifungal Terpenes from Pilgerodendron uviferum (D.DON) Florin", J. Chil. Chem. Soc. V.49 n.2 Concepcion Jun. 2004.
Taylor et al., "Pharmacology and mechanism of action of pregabalin: The calcium channel e-2-δ(alpha2-delta) subunit as a target for antiepileptic drug discovery", Epilepsy Research (2007) 73, 137-150.
Zesiewicz et al., "A pilot, double-blind, placebo-controlled trial of pregabalin (Lyrica) in the treatment of essential tremor"; Movement Disorder 22.11 (2007): 1660-1663. (Abstract only).
Rose et al., Gabapentin: pharmacology and its use in pain management:, Anesthesia, 2002, 57, pp. 451-462.
Gironelli et al., "A Randomized Placebo-Controlled Comparative Trial of Gabapentin and Propranolo in Essential Tremor", Arch Neurol. 1999; 456:475-480.
Spina et al., "Antiepileptic drugs: indications other than epilepsy", Epileptic Disorders: international Epilepsy Journal with videotape 6.2 (2004):57-75. (Abstract only).
Merren, Gabapentin for treatment of pain and tremor: a large case series: Southern Medical Journal 91.8 (1998) 739-744. (Abstract only).
Chawla t al., "Challenges in Polymorphism of Pharmaceuticals," CRIPS, Jan.-Mar. 2004, vol. 5, No. 1, pp. 9-12.
Newman et al., "Solid-state analysis of the active pharmaceutical ingredient in drug products," DDT, Oct. 2003, vol. 8, No. 9, pp. 898-905.
Levitt et al., "Regulation of neocortical interneuron development and the implications for neurodevelopment disorders," Trends in Neurosciences, vol. 27, No. 7, Jul. 2004, pp. 400-406.

"Rose geranium essential oil information" [Online] http://www.essentialoils.co.za/essential-oils/rose-geranium.htm; retrieved Jan. 20, 2010, pp. 1-8.
"Bergamot essential oil information" [Online] http://www.essentialoils.co.za/essential-oils/bergamot.htm; retrieved on Jan. 20, 2010, pp. 1-8.
Jain et al., Essential oil composition of geranium (*Pelargonium* sp.) from the plains of Northern India, Flavour and Fragrance Journal, 2001, pp. 44-46, John Wiley & Sons, Ltd.
Galeotti, Nicoletta et al., Local Anaesthetic Activity of (+)- and (−)-Menthol, Planta Med 67, 2001, pp. 174-176, Georg Thieme Verlag Stuttgart, New York.
Rajeswara, Rao et al., History and botanical nomenclature of rose-scented geranium cultivars grown in India, ResearchGate, Jan. 1992, pp. 155-160.
Lai, Josephine et al., The role of voltage-gated sodium channels in neuropathic pain, Current Opinion in Neurobiology, 2003, pp. 291-297, Elsevier.
Jiro, Imanishi, For Stiff Shoulder or Pain, The Japanese Journal of Clinical Nursing, 2004, pp. 409-416.
Peana et al., "Involvement of adenosine A1 and A2A receptors in (−)-linalool-induced antinocieption," Life Sciences, 78 (2006).
"Lavendar essential oil information" [Online] http://www.essentialoils.co.za/essential-oils.lavendar.htm: retrieved Jan. 20, 2010, pp. 1-8.
Golshani Samira et al., "Antinociceptive effects of the essential oil of Dracocephalum kotschyl in the mouse writhing test"; Journal of Pharmacy & Pharmaceutical Sciences: A Publication of the Canadian Society for Pharmaceutical Sciences, Société Canadienne Des Sciences Pharmaceutiques; Apr. 20, 2004, vol. 7, No. 1, pp. 76-79, XP002564434.
Chang, Tao-Hsin, et al. "Structure of a heterotetrameric geranyl pyrophosphate synthase from mint (*Mentha piperita*) reveals intersubunit regulation." The Plant Cell 22.2 (2010): 454-467.
Anonymous, "Neuragen PM", https://web.archive.org/web/20080723165403/http://www.fottamerica.com/neuragenpn.html, Jul. 23, 2008.

* cited by examiner

COMPOSITIONS COMPRISING TERPENE COMPOUNDS FOR TREATING NEGATIVE SENSORY PHENOMENA

RELATED APPLICATIONS

This application is a 35 U.S.C. §371 filing of International Application Number PCT/CA2009/00114 which was filed on Aug. 13, 2009, which claims priority to U.S. Provisional Application 61/088,508, which was filed on Aug. 13, 2008. The entire contents of the aforementioned applications are hereby incorporated herein by reference.

FIELD OF THE INVENTION

The present invention pertains to the field of compositions and methods for treating sensory deficits. More specifically, the present invention pertains to natural or non-naturally occurring compositions comprising one or more terpene compounds, and methods of using such compositions for the treatment of sensory deficits.

BACKGROUND

Damage or dysfunction of nerves can commonly cause symptoms of sensory deficit or loss. This is sometimes described as "numbness" and may manifest as a decreased ability to sense light touch, pin prick, vibration, hot or cold. Also, stimuli that would normally be painful may be less painful or not illicit pain. Subjects may also experience reduced proprioception. These constellation of symptoms are sometimes labelled "negative sensory phenomena", as distinguished from "positive sensory phenomena" such as allodynia (pain from stimuli not normally painful), dyesthesia (tingling, "pins and needles"), hyperpathia (greatly exaggerated pain sensation to stimuli), hyperesthesia (an increased sensitivity to normal stimulation), dysesthesia (unpleasant abnormal sensations as if damage is being done when this is not the case), and paresthesia (an abnormal sensation whether spontaneous or evoked). Negative motor symptoms such as hypotonia, decreased muscle strength, and decreased endurance may also be present, as well as positive motor symptoms such as increased muscle tone, tremor, dystonia, and dyskinesia.

"Neuropathy" is a term used to describe the condition of damaged nerves. Neuropathic changes are typically produced by damage to, or pathological changes in, the peripheral or central nervous systems. This typically produces pain that is described as "burning", "electric", "tingling", and "shooting" in nature. However, subjects with or without pain often experience negative sensory phenomena (see Bonica's Management of Pain, 3rd ed, ISBN 06833042623). These unwanted and undesirable sensations are often ignored during treatment, due to the lack of effective treatments.

Nociceptive pain usually responds to opioids and non-steroidal anti-inflammatories (NSAIDS), whereas success treating neuropathic pain with these approaches has been limited. Conversely, agents employed to treat neuropathic pain, such as gabapentin, have little or no effect on nociceptive pain. In addition, prior teaching about anesthetics is that negative sensory phenomena are often exacerbated or even induced by analgesic treatment for pain relief.

Thus, current conventional pharmacologic strategies for treating neuropathic pain follow a number of different approaches as outlined below. For the most part, however, the treatment of negative sensory phenomena is ignored. Furthermore, negative sensory phenomenon are often exacerbated by the treatment of pain or in some cases begin at the time of the onset of pain treatment and are considered negative side effects from the treatment of pain. As well, the success of neuropathic pain treatment has been limited due to lack of effectiveness, lack of tolerability of the treatment, or exacerbation or induction of unwanted symptoms.

Antiarrhythmics: Certain antiarrhythmics have sodium-blocking activity. Low-dose IV lidocaine is sometimes used for temporary pain relief from peripheral nervous system injuries, including diabetic neuropathy and postherpetic neuralgia. However, IV lidocaine therapy requires constant monitoring of the patient's ECG and blood pressure to decrease the risk for seizures and arrhythmias. (1)

Antidepressants: Both tricyclic antidepressants and serotonin reuptake inhibitors have been used to treat neuropathic pain. Numerous clinical trials demonstrate the safety and efficacy of TCAs when used to treat either diabetic neuropathy or postherpetic neuralgia, yet response rates have been low at approximately 33%. Amitriptyline was the first tricyclic used to treat neuropathy, and it is still widely prescribed. Amitriptyline has a high incidence of anticholinergic side effects, including delirium in elderly patients. TCAs also have proarrhythmic effects which limit their use in populations with an abnormal EKG. Serotonin specific reuptake inhibitors (SSRIs) have demonstrated less consistent effects on neuropathic pain, relieving neuropathic pain in only one of seven patients. Serotonin noradrenaline reuptake inhibitors have fared slightly better with a response rate of one in every 4-5 neuropathic pain sufferers. (2)

Anticonvulsants: Carbamazepine, phenyloin, gabapentin and lamotrigine have all been used to treat neuropathic pain Inhibition of sodium channel blocking activity by agents such as carbamazepine, phenyloin, and lamotrigine is the proposed mechanism. Studies have shown the anticonvulsant gabapentin to be effective in painful diabetic neuropathy, mixed neuropathies, and postherpetic neuralgia. The most common adverse effects of anticonvulsants in general are sedation and cerebellar symptoms (nystagmus, tremor and incoordination). The most common side effects associated with gabapentin are asthenia, headache, dizziness and somnolence, and in some cases polyneuropathy. Lamotrigine was no better than placebo when used to treat neuropathic pain other than trigeminal neuralgia. (3)

NSAIDS: NSAIDS are not generally recommended first-line agents for treating neuropathic pain. Relief of neuropathic pain with nonsteroidal anti-inflammatory drugs (NSAIDs) is variable. (4)

Opioids: Treatment of neuropathic pain has with opioids has been controversial. Opioids were thought to be ineffective for treating neuropathic pain, but may be somewhat effective for patients who have failed other modalities. Short-term studies provide only equivocal evidence regarding the efficacy of opioids in reducing the intensity of neuropathic pain, while intermediate-term studies demonstrate significant efficacy of opioids over placebo. Reported adverse events of opioids are common and long-term efficacy, safety (including addiction potential), and effects on quality of life need to be further evaluated. Overall, neuropathic pain may be less responsive to opioids than other types of pain. (5)

Other Agents: Baclofen, which blocks both presynaptic and postsynaptic GABA B receptors, is used as a first-line agent to treat trigeminal neuralgia. The most common side effect is drowsiness, and there is concern about possible addictive effects. (6)

Ketamine, an N-methyl-D-aspartic acid (NMDA) receptor antagonist, has garnered increased interest for treating neuropathic pain. Ketamine has been shown to relieve the symptoms of postherpetic neuralgia. However, ketamine causes sedation, slowed reaction times and hallucinations with long-term use. For this reason, it not currently recommended for use in chronic non-malignant pain. (7)

Dextromethorphan is also an NMDA antagonist. It has been used with some success to decrease pain in patients with diabetic neuropathy, but has not benefited those with postherpetic neuralgia, post stroke pain, or peripheral neuropathies other than diabetic. (8).

Topical Agents: Topical agents offer the advantage of local relief without systemic toxicity. Transdermal clonidine has been used with mixed results to treat diabetic neuropathy. Capsaicin cream, which contains an extract of chili peppers, is sometimes used to treat neuropathic pain. It may act on unmyelinated primary afferent nerves by depleting substance P. Depletion requires repeated and consistent use of capsaicin, and patient compliance can be an issue due to the common side effect of an intense burning sensation that decreases with consistent use. Overall, relief with capsaicin cream in clinical trials of neuropathic pain has been inconsistent. (4) Ketamine is a parenteral anesthetic agent that provides analgesic activity at sub-anesthetic doses. It is an N-methyl-D-aspartate (NMDA) receptor antagonist with opioid receptor activity. Controlled studies and case reports on transdermal ketamine demonstrate efficacy in neuropathic pain. (9) Geranium oil, a steam distillate of the geranium plant (*Pelargonium* spp) that is used in flavors and fragrances, is generally regarded as safe by the U.S. Food and Drug Administration. Topical application of geranium oil has been shown to relieve the pain of postherpetic neuralgia in ⅔ subjects, with ¼ of subjects having a dramatic clinical response (10).

Neuropathic symptoms are commonly associated with, but not limited to, a variety of disorders such as diabetes, alcoholism, hypothyroidism, uremia, nutritional deficiencies, chemotherapy, chemical exposure or drug induced, infection, trauma, auto-immune disease, chronic fatigue syndrome, fibromyalgia, ischemia, and inherited disorders. Since neuropathic symptoms are therefore common, and often involve negative as well as positive sensory symptoms, there is the need for new treatments with minimal side effects that give relief from negative sensory symptoms as well as pain. There is also the need for treatments of negative sensory phenomena of an unknown origin.

Natural substances provide a rich diversity of chemical structures, many of which have shown efficacy as therapeutic agents. Many plant derived essential oils have been reported to have beneficial analgesic and anti-inflammatory properties for the treatment of nociceptive pain. For example, a number of species of ginger (*Zingiber* spp.) have been shown to possess antinociceptive properties. Oil of ginger is a complex mixture of constituents, consisting of monoterpenes (phellandrene, camphene, cineole, citral, and borneol), sesquiterpenes (zingiberene, zingiberol, zingiberenol, β-bisabolene, sesquiphellandrene, and others), aldehydes and alcohols (11). Menthol is a common and naturally occurring compound of botanical origin found in plants of the *Mentha* genus which has also been shown to possess analgesic properties with regard to nociceptive pain (12). There has been, however, very little research into plant extracts for the treatment of neuropathy and the associated negative sensory phenomena.

U.S. Pat. Application No. US 2005/0112183 by Galer describes the use of pharmaceutical compounds, preferably benzoic-acid based anesthetics such as lidocaine, to treat neuropathic sensory loss. U.S. Pat. Application No. US 2006/0004050 by Speicher and Kucharik teaches the use of tolperisone for the prevention and treatment of neuropathic symptoms, including pain and negative sensory phenomena. U.S. Patent Application No. US 2003/0092636 by Silberstein teaches the co-administration of anticonvulsants with potassium to prevent and treat neuropathic sensory phenomena, sometimes induced as a side effect of treatment for neuropathic pain.

Geranium oil has been used extensively in perfumery, as an insect repellent, and for other related purposes. For example, U.S. Pat. No. 4,940,583, Thompson, describes the use of geranium oil as a component in an animal repellent composition. U.S. Pat. No. 4,923,685, Forg et al., describes the use of geranium oil as part of a mouth wash composition. U.S. Pat. No. 4,579,677, Hooper et al., describes the use of geranium oil as a scenting agent in a bleaching composition. U.S. Pat. No. 4,311,617, Ansari et al., describes the use of geranium oil in perfumery compositions. U.S. Pat. No. 5,260,313, Frome, entitled "Diagnosis and treatment of various neuralgias," relates to a method of diagnosing and treating neuropathic pain syndromes with a composition of which *Pelargonium graveolens* Ait. oil is the principle therapeutic agent. This essential oil distillate is alternatively called geranium oil bourbon, oil geranium reunion, and oil rose-geranium.

The use of an essential oil distillate geranium oil, however, as taught by Frome, employs a complex mixture of naturally derived compounds, some of which may be effective and some which may be ineffective or which may be irritating or toxic. For example, a number of constituents found in natural geranium oil are known irritants and thereby may cause skin rash when applied topically or even exacerbate pain. For instance a-pinene, a constituent of natural geranium oil, is considered irritating to the skin and exposure can cause rash, burning pain, headache, vomiting and even kidney damage (13). B-phellandrene has known hypersensitizing effects which can cause contact dermatitis (14). P-cymene, another component of natural geranium oil, is also considered a "primary skin irritant", which can cause erythema upon contact and headache, nausea and vomiting if exposure is oral or inhaled (15).

Frome also teaches that the application of geranium oil causes negative sensory symptoms, namely numbness, at the site of application.

Thus, there remains a need for therapies for subjects experiencing negative sensory phenomena, with or without positive sensory phenomena or pain, whether due to nerve cell damage, other pathologies, of unknown cause, or as side effects of medication.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a composition and method for the prevention and treatment of negative sensory phenomena. The composition and method of the present invention have wide ranging applications, such as, but not limited to, the development of therapeutic agents for the treatment of symptoms associated with nerve damage or of unknown origin. These symptoms include, but are not limited to, a decreased ability to sense light touch, pin prick, vibration, hot or cold or reduced proprioception. These symptoms are sometimes referred to as "numbness".

In accordance with one aspect of the present invention, there is provided a composition for the treatment of negative sensory phenomena comprising at least one terpene compound or a combination of terpene compounds and, optionally, one or more pharmaceutically acceptable diluents or excipients.

In accordance with another aspect of the present invention, there is provided a composition for the treatment of negative sensory phenomena comprising one or more compounds of Formula I or Formula II, or a pharmaceutically acceptable isomer, salt, ester or hydrate thereof, Formula I Formula II wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group, or one or more of $R_3$ and $R_4$, $R_5$ and $R_6$, $R_7$ and $R_8$, or $R_{10}$ and $R_{11}$, together form =O, wherein the alkyl, alkoxy, acyloxy and allyl groups are optionally substituted with one or more aryl, amine, amide, halide, phosphate or thiol, and, optionally, one or more pharmaceutically acceptable diluent or excipient.

In accordance with another aspect of the invention, there is provided a method of treating a disorder characterized by negative sensory phenomena due to any cause comprising administering a therapeutically effective amount of a composition as described herein to a mammalian subject, wherein said therapeutically effective amount is an amount that reduces or relieves symptoms or induces changes on clinical testing of nerve function. The mammalian subject is preferably a human. Preferably, the method of the invention is for the treatment of negative sensory phenomena, which can be caused by, for example, diabetic peripheral neuropathy, herpes zoster, post herpetic neuralgia, trigeminal neuralgia, complex regional pain syndrome, reflex sympathetic dystrophy, phantom limb syndrome, chronic disease (multiple sclerosis, HIV, etc), trauma (causalgia), impingement (e.g., sciatica, carpal tunnel, etc), drug exposure, toxic chemical exposure, current infection, past infection, impaired organ function, vascular disease, metabolic disease, cancer, cancer treatment, autoimmune disease, fibromyalgia, or it is idiopathic.

In one preferred embodiment of the invention there is provided a method for the treatment of neuropathic negative sensory phenomena by administering one or more terpene molecules, such as geraniol, citronellol, and related compounds. In particular, the present invention provides a previously unavailable method for treating a range of neuropathic symptoms, through the administration, usually topical or oral administration, to a mammal of a composition comprising one or more terpene molecules, such as geraniol, citronellol, or related compounds, alone or in combination.

DETAILED DESCRIPTION OF THE INVENTION

The present invention provides a novel treatment for symptoms and dysfunction which are often ignored in treatment protocols or are actually exacerbated or even caused by current treatment methods. These symptoms are sometimes classified as negative sensory phenomena, and are often described as "numbness". This may manifest clinically as a decreased ability to sense light touch, pin prick, vibration, hot or cold. Also, stimuli that would normally be painful may be less painful or not illicit pain. Negative sensory phenomena can also manifest as a decreased propioception; which is the sense that indicates to an individual whether their body is moving with required effort, as well as where the various parts of their body are located in relation to each other. These characteristics of negative sensory phenomena can be present with or without positive sensory phenomena, negative motor symptoms, or positive motor symptoms.

In one embodiment of the present invention many of the limitations and drawbacks associated with the prior use of essential oil distillates are overcome by employing isolated and/or purified compounds, and compositions thereof. The use of the isolated and/or purified compounds that are responsible for the desired effect facilitates better control and enhanced therapeutic effect in comparison to use of the same compounds in an unpurified form in a natural oil distillate. Therapeutic agents can therefore be better designed and the quality of these agents controlled by standardizing to the known active ingredients. Compounds that are ineffective, irritating or toxic can be excluded from such synthetic com- positions. Furthermore, the synthetically derived versions of these compounds are more economical to acquire and supply is not affected by climatic conditions or severe weather that often affects medicinal plant production.

The present invention provides a previously unavailable and novel means of restoring or improving sensation by the administration of a composition comprising a compound or mixture of compounds that affect nerve function. The composition of the present invention comprises at least one terpene compound, or a pharmaceutically acceptable salt, ester or solvate thereof, and, optionally, a pharmaceutically acceptable diluent or carrier.

As used herein, the term "terpene compound" is intended to refer to a terpene, a terpenoid, or a pharmaceutically acceptable is salt, ester or solvate thereof. A "terpenoid" is a chemically modified terpene. Examples of terpenoids include, but are not limited to, terpenoid aldehydes, terpenoid acids, terpenoid esters and terpenoid oxides.

In accordance with a specific embodiment of the present invention, the terpene compound in the composition is geraniol, citronellol, geranial, citronellal, linalool, menthone, rose oxide, alpha-terpineol, a pharmaceutically acceptable is salt, ester or solvate thereof, or any mixture thereof.

Preferably the terpene compound has the structure of Formula I or II,

Formula I

Formula II where, $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_3$-$C_{20}$ unbranched allyl group and $C_3$-$C_{20}$ branched allyl group, or one or more of $R_3$ and $R_4$, $R_5$ and $R_6$, $R_7$, and $R_8$, and $R_{10}$ and $R_{11}$ is =O.

wherein the alkyl, alkoxy, acyloxy and allyl groups are optionally substituted with one or more aryl groups, amine groups, amide groups, halides, phosphate groups or thiols.

In accordance with another embodiment of the composition comprises a compound of Formula I or II, wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_{10}$ unbranched alkyl group, $C_1$-$C_{10}$ branched alkyl group, $C_1$-$C_{10}$ unbranched alkoxy group, $C_1$-$C_{10}$ branched alkoxy group, $C_1$-$C_{10}$ unbranched acyloxy group and $C_1$-$C_{10}$ branched acyloxy group, $C_3$-$C_{10}$ unbranched allyl group and $C_3$-$C_{10}$ branched allyl group, or one or more of $R_3$ and $R_4$, $R_5$ and $R_6$, $R_7$, and $R_9$, and $R_{10}$ and $R_{11}$, is =O.

In accordance with another embodiment of the composition comprises a compound of Formula I or II, wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_5$ unbranched alkyl group, $C_1$-$C_5$ branched alkyl group, $C_1$-$C_5$ unbranched alkoxy group, $C_1$-$C_5$ branched alkoxy group, $C_1$-$C_5$ unbranched acyloxy group and $C_1$-$C_5$ branched acyloxy group, $C_3$-$C_5$ unbranched allyl group and $C_3$-$C_5$ branched allyl group, or one or more of $R_3$ and $R_4$, $R_5$ and $R_6$, $R_7$, and $R_8$, and $R_{10}$ and $R_{11}$, is =O.

In accordance with another embodiment of the composition comprises a compound of Formula I, wherein $R_1$, $R_2$, $R_3$, $R_4$, $R_5$, $R_6$, $R_7$, $R_8$, $R_9$ and $R_{12}$ are H and $R_{10}$ and/or $R_{11}$ is selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$) unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group or $R_{10}$ and $R_{11}$ are together =O.

In accordance with a related embodiment, the composition comprises one or more compound of Formula I, which is:

geranial (3,7-dimethyl-2,6-octadienal),
neral (cis 3,7-dimethyl-2,6-octadienal),
geraniol (2,6-Octadien-1-ol, 3,7-dimethyl-, (2E)-),
nerol (cis-3,7-dimethyl-2,6,-octadien-1-ol),
geranyl formate (2,6-Octadien-1-ol, 3,7-dimethyl-, formate, (2E)-),
geranyl butyrate (Butanoic acid, (2E)-3,7-dimethyl-2,6-octadienyl ester),
geranyl tiglate (2-Butenoic acid, 2-methyl-, (2E)-3,7-dimethyl-2,6-octadienyl ester,(2E)-)
or a pharmaceutically acceptable isomer, salt, ester or solvate thereof.

In accordance with one embodiment of the composition comprises a compound of Formula 2, wherein $R_1$, $R_2$, $R_3$, $R_4$, $R_5$, $R_6$, $R_7$, $R_8$, $R_9$, $R_{12}$, $R_{13}$ and $R_{14}$, are H and $R_{10}$ and/or $R_{11}$ is selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group or $R_{10}$ and $R_{11}$ are together =O.

In accordance with a related embodiment, the composition comprises one or more compound of Formula II, which is citronellal (3,7-dimethyl-6-octen-1-al),
citronellol (3,7-dimethyloct-6-en-1-ol),
citronellyl formate (6-Octen-1-ol, 3,7-dimethyl-, formate),
citronellyl butyrate (butanoic acid, 3,7-dimethyl-6-octenyl ester),
citronellyl tiglate (2-Butenoic acid, 2-methyl-, 3,7-dimethyl-6-octenyl ester, (2E)-), or
a pharmaceutically acceptable isomer, salts, ester or solvate thereof.

Specific examples of terpene compounds that can be incorporated in the compositions of the present invention, alone or in combination, are geraniol (2,6-Octadien-1-ol, 3,7-dimethyl-, (2E)-), citronellol (6-Octen-1-ol, 3,7-dimethyl-, (2E)-), and their derivatives. These compounds, alone or in combination, have now been shown to effectively treat negative sensory phenomena.

The terpene compounds of Formula I and Formula II have been found to be useful in treating these often unbearable and untreatable symptoms, often due to neuropathy, which is believed to be caused by aberrant nerve transmission due to damage to nerve tissue. The present invention describes a method of treating negative sensory phenomena using any of a class of aromatic terpene compounds, some of which can be found naturally occurring in *Pelargonium graveolens* Ait. essential oil or other plant sources, or which can be prepared synthetically. In particular, this invention discloses the class and structures of those terpene compounds which can be used to treat negative sensory phenomena.

It is well known that essential oils are complex mixtures of aromatic compounds comprising a broad range of molecular structures including both carbon rings or chains with or without double bonding and with a range of functional side groups. A typical plant essential oil chromatogram may contain in the order of 200 or more distinct peaks. Plant essential oils are a complex mixture of terpenes, sesquiterpenes, esters, alcohols, phenols, aldehydes, ketones, organic acids, and various miscellaneous molecular structures. Furthermore, each class of compound above contains many subclasses. For example, the terpene classification includes hemiterpenes, monoterpenes, diterpenes, sesquiterpenes, triterpenes, tetraterpenes, and associated terpenoids formed by the modification or oxidation of the carbon skeleton. Moreover, any of these compounds may have a wide range of physiological activity in a mammal, and in some cases may show adverse effects or toxicity if applied topically or administered orally. Due to this wide diversity, some of the compounds may even inhibit the effect of nerve transmission inhibition, or may cause an excitation of nerve transmission. Due to the wide range of compounds present, and the extreme complexity of receptor channel pharmacology, it is not obvious to one skilled in the art which compounds have desirable or undesirable effects.

Therefore, in terms of negative sensory phenomena, for example, it would not have been obvious to one skilled in the art, having regard to the previous use of essential oil distillates, that these distillates would provide benefit for negative sensory phenomena. This is particularly illustrated by the fact that Frome (U.S. Pat. No. 5,260,313 referred to above) teaches that application of these compounds causes negative sensory phenomena (referred to by Frome as "numbness"). Furthermore, it would not have been obvious to one skilled in the art which compounds within essential oil distillates have a positive effect, no effect, or even exacerbate negative sensory phenomena. To isolate and determine which compounds are efficacious requires extensive research both on live mammalian subjects and live cell cultures of neuronal tissue.

Furthermore, since the mechanism of negative sensory symptom development and the mechanism of sensory symptom relief are not well understood, it is not obvious to one skilled in the art as to which compounds would have the most effect on the relief of negative sensory symptoms, which compounds may inhibit the relief of negative sensory symptoms, or which compounds may have potential toxicity. It is therefore possible, but not obvious, that identification, purification, and testing of specific compounds found in essential oils may elucidate those compounds responsible for the relief of negative sensory symptoms. Also, in many well documented instances, the elucidation of active drug compounds from medicinal plants is not possible. One common reason for these failed attempts is that the physiological effect of the heterogeneous mixture of compounds found in the naturally derived plant extract or whole plant achieves its effects due to a synergy of compounds. Successive attempts to fractionate heterogeneous mixtures and elucidate one or more distinct active ingredients therefore fail because the synergistic effects of the complex mixture are lost. This phenomena also supports the non-obviousness of the present invention.

In developing the compositions and methods of the present invention, extensive research was carried out using both in vitro and in vivo methods, with the goal of determining the active constituents found in geranium oil and/or other natural and synthetic aromatic oil sources which have a beneficial effect on negative sensory symptoms. Geranium oil is composed of an abundance of chemical entities, many of which are known, but some of which are not yet elucidated. In an effort to determine the active ingredient, or ingredients, in geranium oil, a synthetic blend was provided, which contains known amounts of compounds present in naturally-derived geranium oil, and tested in a patch clamp assay (see Example 1). Individual purified compounds contained within geranium oil were then tested in vivo.

TABLE 1

Example Components of geranium oil blend Analyzed by Gas Chromotography on DB-5 Column

| Identification | % |
| --- | --- |
| *-thujene | 0.11 |
| *-pinene | 1.82 |
| camphene | 0.04 |
| unknown from geranium oil | 0.06 |
| sabinene | 0.08 |
| *-pinene | 1.20 |
| myrcene | 0.45 |
| *-phellandrene | 0.15 |
| *-terpinene | 1.08 |
| p-cymene | 1.22 |
| limonene | 4.66 |
| *-phellandrene** | |
| 1,8-cineole | 12.26 |
| benzyl alcohol | 0.30 |
| cis-*-ocimene | 0.30 |
| trans-*-ocimene | 0.21 |
| *-terpinene | 3.76 |
| linalool oxide fur. trans | 0.11 |
| terpinolene | 0.46 |
| linalool oxide fur. cis | |
| linalool | 17.58 |
| cis-rose oxide | 0.21 |
| trans-rose oxide | 0.07 |
| unknown from lavender oil | 0.09 |
| camphor | 0.61 |
| menthone | 0.20 |
| isomenthone | 2.33 |
| borneol | 0.20 |
| terpin-l-en-4-ol | 7.60 |
| *-terpineol | 1.22 |
| citronellol | 6.23 |
| neral | 0.23 |
| geraniol | 4.42 |
| linalyl acetate | 16.63 |
| geranial | 0.26 |
| citronellyl formate | 2.59 |
| neryl formate | 0.07 |
| lavandulyl acetate | 0.28 |
| geranyl formate | 1.61 |
| citronellyl acetate | 0.15 |
| neryl acetate | 0.20 |
| *-copaene | 0.09 |
| *-bourbonene | 0.24 |
| geranyl acetate | 0.31 |
| cis-*-bergamotene? | 0.66 |
| *-caryophyllene | 0.76 |
| trans* bergamotene ? | 0.17 |

TABLE 1-continued

Example Components of geranium oil blend Analyzed by Gas Chromotography on DB-5 Column

| Identification | % |
| --- | --- |
| *-guaiene? | 0.14 |
| 6,9-guaiadiene | 1.62 |
| cis-*-guaiene | 0.10 |
| citronellyl propionate | 0.11 |
| *-humulene | 0.08 |
| trans-*-farnesene | 0.19 |
| geranyl propionate | 0.42 |
| unidentified | 0.27 |
| bicyclogermacrene | 0.13 |
| *-bisabolene | 0.16 |
| *-cadinene | 0.10 |
| geranyl isobutyrate | 0.10 |
| *-cadinene | 0.31 |
| citronellyl butyrate | 0.14 |
| geranyl butyrate | 0.34 |
| phenylethyl tiglate | 0.17 |
| furanopelargone A | 0.13 |
| geranyl isovalerate | 0.11 |
| citronellyl tiglate | 0.06 |
| geranyl tiglate | 0.40 |
| % Total | 98.36 |

A natural blend of geranium oil and other essential oils (Table 1) was also tested in a panel of human neuropathic pain sufferers, some of whom experienced negative sensory phenomena. As shown in Examples 4, 5, 6 and & 7 relief from negative sensory phenomena was reported sometimes with, and sometimes without, relief from pain. In addition, synthetically produced geraniol was tested in subjects experiencing negative sensory phenomena, with improvements seen in subjectively reported symptoms (see Examples 2 and 3). In addition, microfilament testing revealed improvements in sensory functioning in these subjects. The geranium oil blend or geraniol was topically applied in therapeutically effective amounts to areas of the human body affected with symptoms of negative sensory symptoms. Dosage amount depended on the size of the patient's affected areas. Typically, 1-10 drops were used, 1 drop for smaller affected areas and 10 drops with larger affected areas or areas exhibiting more severe pain symptoms. Once administered, a typical positive response was reported typically within minutes.

A significant number of patients preferred the effects of the synthetic geraniol to geranium oil extracts. This indicates that the synthetic individual compounds offer a distinct advantage over natural geranium oil and geranium oil blends, although both showed efficacy.

The pharmaceutical compositions of the present invention can be prepared using standard, well known techniques. The pharmaceutical compositions of the present invention do not necessarily require inclusion of any pharmaceutically acceptable diluent or excipient. However, such diluents or excipients can be incorporated into the composition as required depending on the desired characteristics of the composition. As used herein, the term "composition" can refer to a pharmaceutical preparation containing a terpene compound alone.

The compositions of the present invention are prepared using isolated or purified terpene compounds, for example, one or more compounds of Formula I or II, or corresponding pharmaceutically acceptable salts, esters or solvates thereof as active components. The term "solvate" is intended to include "hydrate". The compositions of the present invention are not natural oils derived as distillates of plant material, however, the terpene compounds used to prepare the synthetic compositions of the present invention can include one or more compounds that have been isolated from plant material.

The compositions of the present invention can be prepared and administered in a wide variety of dosage forms. The composition of the invention can be in the form of a suspension, pill, gel, oil, cream, patch, spray or aerosol. The composition can be formulated to be suitable for oral administration, topical administration, intranasal delivery, transdermal administration. Processes for manufacture of such compositions are briefly described below, however, the techniques employed in these processes are standard and well known to a worker skilled in the art. It will be obvious to those skilled in the art that the following dosage forms can comprise as the active component, a compound of Formula I or II, a corresponding pharmaceutically acceptable salt, ester or solvate thereof, or any combination thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. Liquid preparations for parenteral injection can be formulated in solution in aqueous polyethylene glycol solution.

Aqueous solutions suitable for oral use can be prepared by dissolving the active component in water and adding suitable colorants, flavours, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

A particularly preferred mode of administration of the composition of the present invention is to a skin surface via a topical route. Such a composition is topically applied in the form of a lotion, solution, cream, ointment or powder. For example, the composition can be formulated into a cream consisting of an aqueous emulsion of polyethylene glycols or liquid paraffin or can be incorporated at a concentration between 1 and 10% into an ointment consisting of a white wax or white soft paraffin base together with such stabilizers and preservatives as may be required. The topical compositions can contain additional ingredients such as binders, excipients, antioxidants, and dyes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted creams, lotions, ointments, tablets, capsules, or powders in tubes, vials or ampoules. Also, the unit dosage form can be a capsule, tablet, cachet, or lozenge itself, or it can be the appropriate number of any of these in packaged form.

The quantity of active component in a unit dose preparation can be varied or adjusted according to the particular application and the potency of the active component. The dosages, however, can be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

To gain a better understanding of the invention described herein, the following examples are set forth. It should be understood that these examples are for illustrative purposes only. Therefore, they should not limit the scope of this invention in any way.

EXAMPLES

Example 1

Patch Clamp Electrophysiological Studies of Mouse Hippocampal Slices

Studies were conducted on mouse hippocampal brain slice preparations. In terms of the slice preparations, 200-400 µM coronal brain slices were prepared from animals housed in a 12 hour light (ZT 0-12):12 hour dark (ZT 12-24) environment. Animals were anesthetized with isoflurane, decapitated, the brain rapidly removed and placed in ice cold, oxygenated (95% $O_2$:5% $CO_2$), bicarbonate-buffered artificial cerebral spinal fluid (ACSF). A 1 $cm^2$ block of brain tissue containing the hippocampi was glued to a cutting surface and coronal slices were prepared using a Leica VT1000S microtome (Leica Microsystems). All slices were left to equilibrate for approximately one hour prior to the transfer to a recording chamber. Once transferred to the chamber, slices were continuously superfused with oxygenated ACSF at a rate of 3 ml/min @30° C. and recordings are generally made for the next 6-12 hours. Patch microelectrodes (5-8 MΩ) made from borosilicate glass (Garner Glass Co.) and filled with $K^+$ based internal patch solution composed of: (in mM) 120 K-acetate, 40 HEPES, 10 EGTA, 6 $MgCl_2$, nystatin (450 µg/ml) or gramicidin B (5 µg/ml) and pluronic acid F127.

The perforated patch recording technique and will be used (Korn & Horn, 1989) and viable Hippocampal neurons were visually targeted using Infrared Differential Interference Contrast (IR-DIC) microscopy using a Leica DM LFSA scope. The perforated patch configuration provides access resistances to the cell comparable to conventional whole cell recordings and such access is generally obtained 2-15 minutes after gigaohm seals are formed. Recordings were made from 3 different patch rigs equipped with either Axopatch 700B patch clamp amplifiers interfaced via a Digidata 1322A to a PC computer or on, in terms of the studies performed on dissociated DRG neurons, a Zeiss Axoscop 200 inverted microscope equipped with an Axopatch 200B/Digidata 1322A using Pclamp 9.0 and Axoscope 9 software.

Test compounds were bath-applied by superfusion to examine for changes in excitability and/or attenuation of ion channels and the effects of compounds on evoked synaptic responses. Stimulating electrodes (concentric or bipolar) were placed within the slices and in accordance with the well known fiber tract pathways of passage for the DH and the hippocampus.

Figure 2:
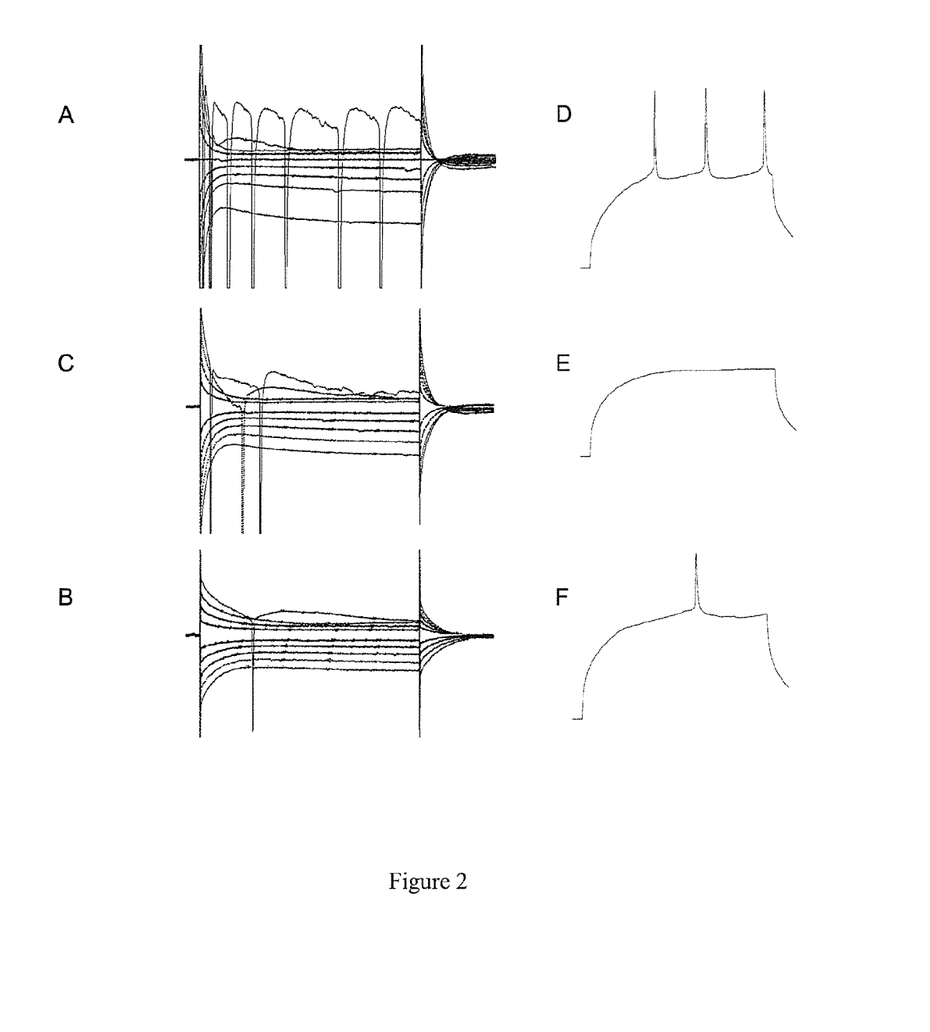
FIG. 2 depicts typical current voltage relationship in a cortical neuron (A=Control: B=Geraniol: C=After Washout) and the typical response of a cortical neuron following depolarizing current pulse (D=Control condition: E=in the presence of geraniol: F=After recovery).

Typical current-voltage (I-V) relation in a cortical neuron is shown in FIGS. 2A, 2B, and 2C. Superimposed responses to a series of 10 mV steps (250 ms) ranged from −110 to −20 mV are shown, (A) in control condition, (B) in presence of geraniol, and (C) after washout of the drug. Note the reduction in the membrane current amplitude and the inhibition of action potentials in presence of geraniol.

Typical response of a cortical neuron following a depolarizing current pulse of 0.4 nA is shown in FIGS. 2D, 2E and 2F, (D) in control condition, (E) in presence of geraniol, and (F) after recovery. Note the inhibition of action potential in presence of the tested compound.

Figure 1:
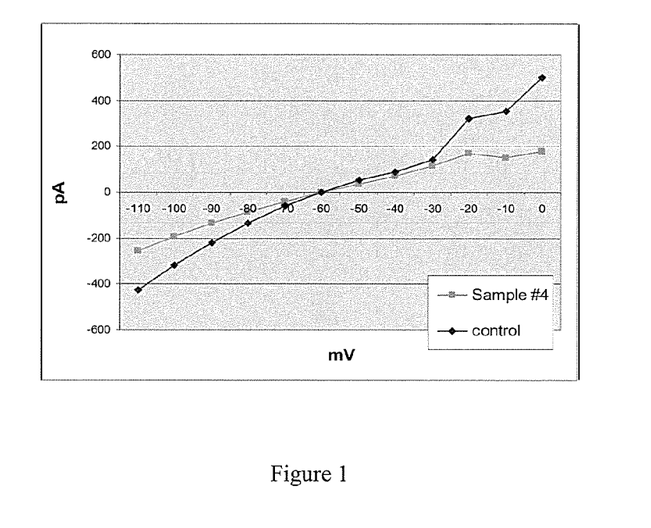
FIG. 1 depicts current-voltage plots obtained from patch clamp electrophysiological studies of mouse hippocampal slices using sample #4 (Geraniol) and a Control, which demonstrate a reduction of membrane currents (geraniol vs. control).

Mean current-voltage plots for 6 cortical neurons are plotted in FIG. 1. Note the reduction of membrane currents in the presence of geraniol (test compound #4).

Figure 3:
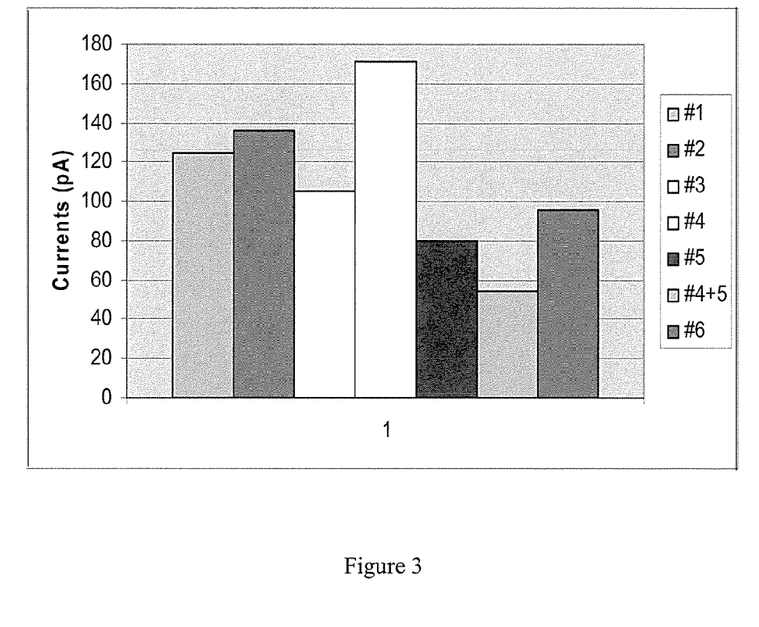
FIG. 3 graphically demonstrates the net current reduction in the presence of various treatments during patch clamp testing.

FIG. 3 shows the net current reduction in the presence of various naturally-derived geranium essential oils, and pure compounds, for each tested drug following the most negative voltage step (−110 mV). Samples 1, 2 and 6 are examples of naturally-derived geranium oils; sample 3 is a synthetic composition, sample 4 is pure geraniol, sample 5 is pure citronellol and sample 4+5 is 50:50 (by volume) combination of geraniol and citronellol. Net current represents the difference between current measured in control condition and in presence of tested compound, in response to the same voltage step. Note that of the compounds tested, sample #4 (geraniol) resulted in the greatest inhibition (current differential between control and tested compound).

The data provided in this example suggests that the compounds and compositions tested are useful in treatment of a disorders associated with aberrant nerve function.

Example 2

Case Study

DB is a 73 year old male who has impaired glucose tolerance, but not diabetes. He is participating in a study to prevent the conversion to diabetes using lifestyle modification. His waist is 99 cm and his weight is 86.4 kg.

He takes Benzepril (an ACE inhibitor) and Felodipine (a calcium channel blocker) for hypertension. He also takes hyoscyamine and diphenoxylate with atropine for irritable bowel syndrome.

He was seen for his study visit on Mar. 7, 2008 and complained of numbness on the soles of his feet. His sensation was tested with a nylon filament and the patient could not feel the filament on the ball of either foot. Geraniol was applied to the ball of one foot. After approximately 5 minutes the feet were retested with the nylon filament. The foot that had not been treated still could not detect the touch of the filament. The foot treated with topical geraniol was able to feel the nylon filament.

Example 3

Case Study

GJ is an 84 year old male with idiopathic neuropathy who had numbness in both feet. He is 177.8 cm tall, his weight is 72.2 kg and his BMI is 23 kg/m$^2$. He takes viokase, levoxyl, digitek, allopurinol, nexium, metoprolol, coumadin and a multivitamin.

He was seen for the first time May 3, 2008 complaining of numbness on the soles of his feet. He could not feel a nylon filament used to test sensation on the bottom of either foot. He had geraniol applied to the left foot and the sensation was retested after 5 minutes. On retesting the patient could detect feeling with a nylon filament on the sole of the left foot treated with geraniol, but was unable to feel it on the right foot that had no application of geraniol. The patient was given geraniol to use on the left foot every other day. He returned in two weeks and said that his left foot continued to have more feeling than the right foot over the 2 week period.

Example 4

Case Study

JH is a 47 year old male with the chief complaint of migraine headaches. The headaches are typically treated with Imitrex (sumatriptan). In addition, to treat the migraine headaches he began applying a blend of natural essential oils containing geranium (Table 1). The subject reported persistent numbness of the second digit (index finger) of his right hand due to a knife would ten years previous. He reported relief of his numbness and return of normal sensations for the first time in ten years after using his index finger to apply the essential oils to his temple. This was an unexpected effect according to the subject.

Example 5

Case Study

A 65 yr old Caucasian female diagnosed with Type 2 diabetes and peripheral neuropathy with pain and numbness in feet and toes for 1 year. Her diabetic diagnosis was less than 5 years previous, and she reported experiencing pain, tingling, and numbness several times per week. She applied a few drops of the geranium oil blend (Table 1) to her feet and reported no change in pain but almost immediate relief of the numbness in her toes. She said it was like "having life in her toes again", indicating a return of sensation and proprioception. She has reapplied the topical geranium oil blend and has longer and longer periods of restored sensation, lasting for a full day after a few applications.

Example 6

Case Study

A 54 yr old Hispanic male reported pain and numbness in feet due to Type 1 diabetes of ten years duration. He reported daily pain at a level of 4/10. He applied a few drops of the geranium oil blend (Table 1) to his feet and reported that in about 10 minutes the pain and numbness was completely gone and for the first time in years he slept through the night.

Example 7

Case Study

A 62 yr old female Caucasian with pain and numbness in her hands due to Type 2 diabetes of 7 yrs duration. Pain had started 1 year previous. She reported numbness in both hands and applied a few drops of the geranium oil blend (Table 1) to both hands. Her pain and numbness was completely relieved in 15 minutes. On another occasion she repeated the treatment and again obtained complete relief of pain and numbness.

REFERENCES

1. Kalso, E Sodium Channel Blockers in Neuropathic Pain, Current Pharmaceutical Design, Volume 11, Number 23, September 2005, pp. 3005-3011(7).
2. Sindrup, Søren H.; Otto, Marit; Finnerup, Nanna B. Jensen, Troels S. Antidepressants in the Treatment of Neuropathic Pain Basic & Clinical Pharmacology & Toxicology, Volume 96, Number 6, June 2005, pp. 399-409(11).
3. Jensen T S. Anticonvulsants in neuropathic pain: rationale and clinical evidence. Eur J Pain. 2002; 6 Suppl A:61-8.
4. Kingery W S. A critical review of controlled clinical trials for peripheral neuropathic pain and complex regional pain syndromes. Pain 1997; 73:123-139.
5. Elon Eisenberg, Md.; Ewan D. McNicol, RPh; Daniel B. Carr, M D Efficacy and Safety of Opioid Agonists in the Treatment of Neuropathic Pain of Nonmalignant Origin *JAMA*. 2005; 293:3043-3052.
6. Fromm G H. Baclofen as an adjuvant analgesic. J Pain Symptom Management 1994; 9(8):500-509.
7. Eide K, Stubhaug A, Oye I, Breivik H. Continuous subcutaneous administration of the N-methyl-D-aspartic acid (NMDA) receptor antagonist ketamine in the treatment of postherpetic neuralgia. Pain 1995; 61(2):221-8.
8. Sindrup S H, Jensen T S. Efficacy of pharmacological treatments of neuropathic pain: an update and effect related to mechanism of drug action. Pain 1999; 83(3):389-400.
9. Kronenberg R H. Ketamine as an analgesic: parenteral, oral, rectal, subcutaneous, transdermal and intranasal administration. J Pain Palliat Care Pharmacother. 2002; 16(3):27-35.
10. Greenway F L, Frome B M, Engels T M 3rd, McLellan A. Temporary relief of postherpetic neuralgia pain with topical geranium oil. Am J Med 2003 November; 115(7):586-7.
11. Vendruscolo A, Takaki I, Bersani-Amado L E, Dantas J A, Bersani-Amado C A, Cuman R K. N Antiinflammatory and antinociceptive activities of zingiber officinale roscoe essential oil in experimental animal models. Ind J Pharm Vol 38 No 1 Pg 58-59 2006.
12. Nicoletta Galeotti, Lorenzo Di Cesare Mannelli, Gabriela Mazzanti, Alessandro Bartolini, Carla Ghelardini Menthol: a natural analgesic compound Neuroscience Letters 322 (2002)145-148 NEUROLOGY 2005; 65:812-819.
13. New Jersey Dept of Health Hazardous Substance Fact Sheet July 1999#0052.
14. http://Toxnet.nlm.nih.gov CASRN:555-10-2.

15. Johnston, G. A. R. GABA Receptor Channel Pharmacology. Current Pharmaceutical Design 2005, 11, 1867-1885.

U.S. Patent Documents

| | | |
|---|---|---|
| US 2005/0112183 | May 2005 | Galer |
| US 2006/0004050 | January 2006 | Speicher/Kucharik |
| US 2003/0092636 | May 2003 | Silberstein |
| 4,311,617 | January 1982 | Ansari |
| 4,579,677 | July 1986 | Hooper |
| 4,923,685 | May 1990 | Wuelkhitz |
| 4,940,583 | July 1990 | Thompson |
| 5,260,313 | November 1993 | Frome |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The scope of the invention should be determined by the appended claims and their legal equivalents, rather than by those presented in the in vitro or in vivo studies or by the examples given. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method of treating negative sensory phenomena in a mammalian subject, comprising
    administering a therapeutic amount of at least one terpene compound to said mammalian subject,
    wherein the therapeutic amount inhibits nerve transmission and reduces the negative sensory phenomena in the subject, wherein the terpene compound is purified, and/or synthetic, and wherein the terpene compound is selected from the group consisting of geraniol, citronellol, combinations thereof, and pharmaceutically acceptable isomers, salts, esters and solvates thereof.

2. The method as defined in claim 1, wherein said terpene compound is administered in combination with one or more pharmaceutically acceptable diluents or excipients.

3. The method as defined in claim 1, wherein said terpene compound is geraniol or a pharmaceutically acceptable salt thereof.

4. The method as defined in claim 1, wherein said terpene compound is geraniol in combination with citronellol
    and, optionally, one or more pharmaceutically acceptable diluent or excipient.

5. The method as defined in claim 1, wherein the mammalian subject is a human.

6. The method as defined in claim 1, wherein the terpene compound or combination of terpene compounds is in a composition in the form of a suspension, pill, gel, oil, cream, patch, spray or aerosol.

7. The method as defined in claim 6, wherein the composition is suitable for oral administration, topical administration, intranasal delivery, or transdermal administration.

8. The method as defined in claim 1, wherein the cause of the negative sensory phenomena is due to neuropathy.

9. The method as defined in claim 8, wherein said neuropathy is caused by diabetic peripheral neuropathy, herpes zoster, post herpetic neuralgia, trigeminal neuralgia, complex regional pain syndrome, reflex sympathetic dystrophy, phantom limb syndrome, chronic disease (multiple sclerosis, HIV, etc), trauma (causalgia), impingement (e.g., sciatica, carpal tunnel, etc), drug exposure, toxic chemical exposure, current infection, past infection, impaired organ function, vascular disease, metabolic disease, cancer, cancer treatment, autoimmune disease, fibromylagia, or it is idiopathic.

10. The method as defined in claim 1, wherein the negative sensory phenomena are characterized by a decreased ability to sense at least one of light touch, pin prick, vibration, hot, cold or pain and/or a reduced proprioception.

* * * * *